United States Patent
Kim et al.

(10) Patent No.: US 9,919,260 B2
(45) Date of Patent: Mar. 20, 2018

(54) METHOD OF RECOVERING ABSORPTION SOLVENT IN BUTADIENE PRODUCTION PROCESS BY OXIDATIVE DEHYDROGENATION

(71) Applicant: LG CHEM, LTD., Seoul (KR)

(72) Inventors: Dae Hyeon Kim, Daejeon (KR); Jeong Seok Lee, Daejeon (KR); Mi Kyung Kim, Daejeon (KR); Jae IK Lee, Daejeon (KR); Jong Ku Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 349 days.

(21) Appl. No.: 14/426,919

(22) PCT Filed: Nov. 21, 2014

(86) PCT No.: PCT/KR2014/011286
§ 371 (c)(1),
(2) Date: Mar. 9, 2015

(87) PCT Pub. No.: WO2015/076624
PCT Pub. Date: May 28, 2015

(65) Prior Publication Data
US 2016/0256815 A1    Sep. 8, 2016

(30) Foreign Application Priority Data

Nov. 22, 2013 (KR) .......... 10-2013-0143115
Nov. 21, 2014 (KR) .......... 10-2014-0163617

(51) Int. Cl.
*B01D 11/04* (2006.01)
*B01D 53/14* (2006.01)
(Continued)

(52) U.S. Cl.
CPC ...... *B01D 53/1425* (2013.01); *B01D 11/0488* (2013.01); *B01D 53/1418* (2013.01);
(Continued)

(58) Field of Classification Search
CPC ..... B01D 11/00; B01D 11/04; B01D 11/0426; B01D 11/043; B01D 11/0488;
(Continued)

(56) References Cited

U.S. PATENT DOCUMENTS 3,364,988 A * 1/1968 Fortunat Hartmann . B01D 3/20
165/85
3,663,641 A * 5/1972 Hanson ...................... C07C 7/10
585/864
(Continued)

FOREIGN PATENT DOCUMENTS

CN          1160283 C       8/2004
CN        201586478 U       9/2010
(Continued)

OTHER PUBLICATIONS

"Separation and preparation of butadience," Foreign Petrochemical Industry, Shanghai Institute of Science and Technology Information Press: 4-9 (1971).

*Primary Examiner* — Joseph Drodge
(74) *Attorney, Agent, or Firm* — Dentons US LLP

(57) ABSTRACT

The present invention relates to a method of recovering an absorption solvent in a butadiene production process through oxidative dehydrogenation, the method including: a) transferring a light gas discharged from an upper portion of an absorption tower to a wash column; and b) recovering the absorption solvent included in the light gas by a solvent circulating in the wash column. Since an absorption solvent may be prevented from being introduced into a reactor, or being discharged to an outside of a system, economic efficiency of a butadiene production process is improved.

7 Claims, 1 Drawing Sheet

(51) Int. Cl.
*C07C 7/11* (2006.01)
*C07C 5/48* (2006.01)
*C07C 11/16* (2006.01)
*C07C 5/32* (2006.01)

(52) U.S. Cl.
CPC ............ *B01D 53/1487* (2013.01); *C07C 5/32* (2013.01); *C07C 5/48* (2013.01); *C07C 7/11* (2013.01); *B01D 53/1493* (2013.01); *B01D 2252/20405* (2013.01); *B01D 2252/20431* (2013.01); *B01D 2257/7022* (2013.01)

(58) Field of Classification Search
CPC ............... B01D 11/0492; B01D 53/14; B01D 53/1418; B01D 53/1425; B01D 53/1487; B01D 53/1493; B01D 2011/002; B01D 2257/702; B01D 2257/7022; B01D 2252/20; B01D 2252/20405; B01D 2252/20431; B01D 2252/50; B01D 2252/504; C07C 7/04; C07C 7/005; C07C 7/08; C07C 7/11; C07C 5/42; C07C 5/48; C07C 11/12; C07C 11/16; C07C 11/167; C07C 2523/18; C07C 2523/28; C07C 2523/31; C07C 5/32; C07C 5/327; C07C 5/333; B01J 8/00; B01J 19/00; B01J 2219/00452
USPC ... 95/49, 174, 177, 179, 186, 187, 188, 190, 95/237, 239, 240; 96/243, 267, 351; 210/511, 634, 749, 757; 585/616–633, 585/654, 655, 659, 833, 834, 860, 864, 585/504, 507, 508, 615; 422/129, 608
See application file for complete search history.

(56) References Cited

U.S. PATENT DOCUMENTS

| | | | |
|---|---|---|---|
| 4,436,707 A * | 3/1984 | Karwat | B01D 53/1456 423/226 |
| 4,504,692 A | 3/1985 | Arakawa et al. | |
| 6,337,429 B1 | 1/2002 | Kindler et al. | |
| 2002/0052533 A1* | 5/2002 | Koga | C10G 7/08 585/313 |
| 2008/0183024 A1* | 7/2008 | Klanner | C07C 5/3337 585/633 |
| 2010/0048960 A1* | 2/2010 | Degen | C07C 29/095 568/904 |
| 2011/0158891 A1 | 6/2011 | Nagayasu et al. | |
| 2012/0130137 A1 | 5/2012 | Orita et al. | |
| 2012/0226087 A1* | 9/2012 | Kostova | C07C 7/04 585/810 |
| 2013/0164203 A1 | 6/2013 | Nagayasu et al. | |
| 2013/0211166 A1* | 8/2013 | Giesa | C07C 7/11 585/324 |
| 2013/0284021 A1 | 10/2013 | Miyamoto | |
| 2014/0081062 A1* | 3/2014 | Rezai | C07C 7/14841 585/326 |
| 2016/0289145 A1* | 10/2016 | Lee | C07C 7/005 |
| 2016/0326707 A1* | 11/2016 | Khachaturian | E02B 17/0809 |

FOREIGN PATENT DOCUMENTS

| | | |
|---|---|---|
| CN | 102863309 A | 1/2013 |
| EP | 2338583 A2 | 6/2011 |
| EP | 2644255 A1 | 2/2013 |
| JP | S48-010778 B | 4/1973 |
| JP | S48-54019 A | 7/1973 |
| JP | S59-167525 A | 9/1984 |
| JP | 2003128595 A | 5/2003 |
| JP | 2005238220 A | 9/2005 |
| JP | 2010275210 A | 12/2010 |
| JP | 2011006395 A | 1/2011 |
| JP | 2012111751 A | 6/2012 |
| KR | 10-2001-0043057 A | 5/2001 |
| KR | 10-2012-0103759 A | 9/2012 |
| WO | 2010137595 A1 | 2/2010 |
| WO | 2012-131016 A1 | 4/2012 |
| WO | 2014-148323 A1 | 9/2014 |

* cited by examiner

US 9,919,260 B2

METHOD OF RECOVERING ABSORPTION SOLVENT IN BUTADIENE PRODUCTION PROCESS BY OXIDATIVE DEHYDROGENATION

This application is a National Stage Entry of International Application No. PCT/KR2014/011286, filed on Nov. 21, 2014, which claims priority to and the benefit of Korean Patent Application No. 10-2013-0143115, filed on Nov. 22, 2013 and Korean Patent Application No. 10-2014-0163617 filed on Nov. 21, 2014, all of which are incorporated herein by reference in their entirety.

TECHNICAL FIELD

The present invention relates to a method of recovering an absorption solvent in a butadiene production process by oxidative dehydrogenation.

BACKGROUND ART

Butadiene is an important basic chemical and is used as an intermediate in a number of petrochemical products, such as a synthetic rubber and an electronic material, and demand and value of butadiene as one of the most important feedstocks in a current petrochemical market are gradually increasing.

Methods of producing butadiene include a method extracting butadiene from a C4 oil component through naphtha cracking, a method through direct dehydrogenation of normal butene (n-butene), a method through oxidative dehydrogenation of n-butene, and the like.

In the butadiene production method through oxidative dehydrogenation of butane or butene among the above methods, nitrogen, stream, and the like as well as raw materials are supplied in order to reduce explosion risk of reactants, to prevent a catalyst from coking, and to remove heat of reaction. By the reaction, a main product of butadiene is first produced and byproducts of carbon monoxide, carbon dioxide and the like are secondarily produced.

By separating and removing a light gas from the reaction products, a C4 mixture including butadiene is obtained, and by refining the C4 mixture, high purity butadiene is obtained. Meanwhile, a part or the whole of the separated and removed light gas may be recycled.

DISCLOSURE OF THE INVENTION

Technical Problem

The light gas produced during oxidative dehydrogenation of butane or butene is discharged to an upper portion of a solvent absorption tower, in which a part of the discharged light gas is circulated and re-introduced into a reactor, and the rest is included in a purge stream and discharged to an outside of the system.

A part of the absorption solvent used in the solvent absorption tower may be included in the light gas, and the absorption solvent is introduced in the reactor to have a bad influence on oxidative dehydrogenation or is included in the purge stream and discharged, thus having a problem of causing a loss.

Accordingly, the present invention aims at providing a process of recovering an absorption solvent discharged together with a light gas by being provided with a wash column connected to an upper portion of the absorption tower through which the light gas is discharged.

Technical Solution

According to an aspect of the present invention, there is provided a method of recovering an absorption solvent in a butadiene production process through oxidative dehydrogenation, the method including: a) transferring a light gas discharged from an upper portion of an absorption tower to a wash column; and b) recovering the absorption solvent included in the light gas by a solvent circulating in the wash column.

According to another aspect of the present invention, there is provided an apparatus of recovering an absorption solvent, the apparatus including: a pipe through which a light gas is transferred from an absorption tower; a wash column connected to the pipe; and a pump provided on one side of the wash column to circulate a solvent introduced into the wash column.

Advantageous Effects

According to the present invention, an absorption solvent discharged together with a light gas may be recovered, thus preventing the absorption solvent from being introduced into a reactor to have a bad influence on oxidative dehydrogenation.

Further, according to the present invention, since the absorption solvent may be prevented from being discharged to an outside of a system and lost, process economics may be secured.

MODE FOR CARRYING OUT THE INVENTION

Figure 1:
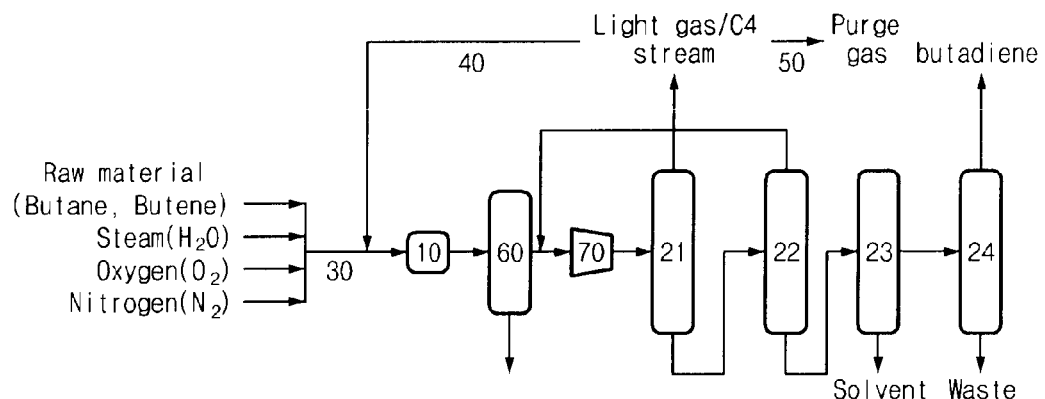
FIG. 1 schematically illustrates a butadiene production process by using general oxidative dehydrogenation.

Hereinafter, preferred embodiments of the present invention will be described with reference to the attached drawings. Although the present invention will be described with respect to the embodiments illustrated in the drawings, it should be noted that the embodiments are provided only for illustration and are not intended to limit the technical spirit and the core elements and operations of the present invention.

In particular, it should be understood that the term "light gas" used throughout the present specification including claims and abstract indicates a gas component including nitrogen, oxygen, steam, carbon monoxide or carbon dioxide, etc. among reaction products produced through oxidation dehydrogenation. In addition, it should be understood that the term "active component" indicates a component, such as nitrogen, oxygen, an unreacted raw material, or butadiene, active in a butadiene-producing reaction.

Butadiene Production Apparatus

A butadiene production apparatus for carrying out a butadiene production method through the above-described oxidative dehydrogenation may include separate pipelines for allowing components of first flow 30 including a C4 oil component, steam, oxygen ($O_2$), and nitrogen ($N_2$) to be respectably introduced into a reactor 10, or a plurality of separate pipelines which are branched from one pipe line directly connected to the reactor 10 and through which the components included in the first flow are separately supplied (See FIG. 1).

In addition, the apparatus includes the reactor 10 connected to the pipeline and in which oxidation dehydrogenation takes place. The apparatus may further include a mixing device disposed in front of the reactor 10 to mix the components included in the first flow before being introduced into the reactor (See FIG. 1).

Further, the apparatus may include a gas separation device for separating a C4 mixture including butadiene obtained from the reactor 10 from a light gas and including at least one of a solvent absorption tower 21 and a degassing column 22 (See FIG. 1).

To obtain high purity butadiene, the apparatus may also include a solvent recovery unit 23 and a butadiene refining unit 24 (see FIG. 1).

Meanwhile, the butadiene production apparatus of the present invention may further include an inert recycle line allowing a second flow 40 including one or more of nitrogen ($N_2$) and carbon dioxide ($CO_2$) among the light gases separated from the gas separation device to be re-introduced into the reactor, and a discharge line for discharging a third flow 50 including purge to an outside of the system (See FIG. 1).

Further, the apparatus may further include, between the reactor and the gas separation device, a quenching device including a quenching tower 60 for cooling a reaction product obtained from the reactor, a compressor 70 for compressing the reaction product, and a dehydration device for removing moisture included in the reaction product.

Meanwhile, an upper portion (the top) of the solvent absorption tower may be connected to a wash column 45. In the wash column, a process of recovering the absorption solvent discharged together with the light gas may proceed (see FIG. 2).

Butadiene Production Process

First, a first flow 30 including a C4 oil component, steam, oxygen ($O_2$), and nitrogen ($N_2$) is introduced into a reactor to proceed oxidative dehydrogenation.

The C4 oil component may mean C4 raffinate-1,2,3 remained after useful compounds are separated from a C4 mixture produced by naphtha cracking, and may mean C4s which may be obtained through ethylene dimerization. In an embodiment of the present invention, the C4 oil component may be one or a mixture of two or more selected from the group consisting of n-a butane, trans-2-butene, cis-2-butene, and 1-butene.

In the oxidative dehydrogenation, the steam or nitrogen ($N_2$) is a diluent gas introduced into the reactor for the purpose of reducing explosion risk of a reactant, preventing a catalyst from coking, and removing heat of reaction.

Meanwhile, oxygen ($O_2$) as an oxidant reacts with the C4 oil component to cause dehydrogenation.

In an embodiment of the present invention, the first flow 30 may be a flow in which a C4 oil component, steam, oxygen (O2) and nitrogen ($N_2$) are introduced into the reactor through separate pipelines.

On the other hand, in another embodiment of the present invention, the first flow 30 may be a flow in which a C4 oil component, steam, oxygen ($O_2$), and nitrogen ($N_2$) pass through a plurality of separate pipelines branched from one pipeline directly connected to the reactor, are mixed in the one pipeline or mixed by a mixing device disposed in front of the reactor, and then are introduced into the reactor.

In an embodiment of the present invention, the C4 component, steam, oxygen ($O_2$), and nitrogen ($N_2$) included in the first flow may be supplied into the pipeline in a gas state, and the gases may be preheated at a favorable temperature for oxidative dehydrogenation and then be introduced.

In an embodiment of the present invention, the catalyst filled in the reactor is not particularly limited if the catalyst allows the C4 oil to undergo oxidative dehydrogenation to produce butadiene, and may be, for example, a ferrite-based catalyst or a bismuth molybdate-based catalyst.

In an embodiment of the present invention, the catalyst may be a bismuth molybdate-based catalyst, and the bismuth molybdate-based catalyst may include one or more selected from the group consisting of bismuth, molybdenum, and cobalt, and also the bismuth molybdate-based catalyst may be a multi-component bismuth molybdate catalyst. However, the type and amount of the reaction catalyst may vary according to a specific condition of a reaction.

In an embodiment of the present invention, the reactor 10 is not particularly limited if oxidative dehydrogenation may proceed. For example, the reactor 10 may be a tubular reactor, a tank reactor, or a fluidized bed reactor. As another example, the reactor may be a fixed bed reactor, and may be a fixed bed multi-tubular reactor or a plate type reactor.

As described above, when the first flow 30 including the C4 oil component, steam, oxygen ($O_2$), and nitrogen ($N_2$) are introduced into the reactor 10 filled with the catalyst, oxidative dehydrogenation proceeds. The oxidative dehydrogenation is an exothermic reaction, and has a main reaction formula expressed as the following reaction formula 1 or 2.

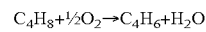

$$C_4H_8 + \tfrac{1}{2}O_2 \rightarrow C_4H_6 + H_2O \qquad \text{Reaction Formula 1}$$

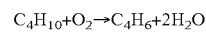

$$C_4H_{10} + O_2 \rightarrow C_4H_6 + 2H_2O \qquad \text{Reaction Formula 2}$$

Hydrogen is removed from butane or butene by the oxidative dehydrogenation to produce butadiene. Meanwhile, the oxidative dehydrogenation is accompanied by a side reaction in addition to the main reaction of the chemical formula 1 or 2, and the side reaction may produce side reaction products including a low boiling point and water-soluble by-product, such as carbon monoxide (CO), carbon dioxide ($CO_2$), acetylenes or carbonyls, and a high boiling point by-product, such as phenol and coumarin. The side reaction product should be separated and discharged to an outside of the system so that continuous accumulation does not occur in a process.

Meanwhile, the C4 mixture including butadiene obtained from the reactor may be further subject to a post-treatment process for obtaining high purity butadiene. The post-treatment process may include one or more steps selected from the group consisting of a quenching step using a plurality of quenching towers, a compression step using a compressor, a dehydration step using a dehydration device, a gas separation step using a gas separation device, and a refining step using a solvent separation and recovering device and a refining tower.

Quenching Step

In an embodiment of the present invention, a reaction product obtained from the reactor may be subjected to a quenching step.

The reaction product obtained from the reactor may be in a form of a high temperature gas, and accordingly needs to be cooled before being supplied to the gas separation device.

A cooling method used in the quenching step is not particularly limited. For example, a cooling method bringing a cooling solvent into direct contact with the reaction product may be used and a cooling method bringing a cooling solvent into indirect contact with the reaction product may be used.

Dehydration Step

In an embodiment of the present invention, a dehydration step removing moisture from the reaction product obtained from the reactor may be further included.

When moisture remains in the reaction product, the remaining moisture may cause a machine to be corroded or an impurity to be accumulated in a solvent in subsequent steps such as solvent absorption, separation, and refining steps, and accordingly, the moisture should be removed.

A dehydration method in the dehydration step is not particularly limited. Further, a dehydration means used in the dehydration step is not particularly limited, but the dehydration means may be a desiccant (moisture adsorbent), such as calcium oxide, calcium chloride, a molecular sieve. The molecular sieve among the dehydration means may be advantageous in terms of easy reproduction, easy handling and the like.

Gas Separation Step

In an embodiment of the present invention, the reaction product obtained from the reactor is brought into contact with an absorption solvent in a solvent absorption tower, so that only the C4 mixture including butadiene is selectively absorbed by the absorption solvent and the remaining light gases are separated and removed.

In detail, when the reaction product obtained from the reactor comes into countercurrent contact with the absorption solvent in the absorption tower, the C4 mixture including butadiene is selectively absorbed by the absorption solvent, and the remaining light gases are discharged via a pipe from the top of the absorption tower.

A type of the absorption tower is not particularly limited, but the absorption tower may be, for example, a packed column, a wetted-wall tower, a spray tower, a cyclone scrubber, a bubble tower, a bubble agitation tank, a plate tower (a bubble cap tower, a perforated plate tower), or a foam separation tower.

The absorption solvent may be an absorption solvent commonly used in the technical field, for example, a C6-C10 saturated hydrocarbon, a C6-C8 aromatic hydrocarbon, an amide compound of C6 to C8, or the like.

In addition, the absorption solvent may be a polar aprotic solvent, for example, one or a mixture of two or more selected from the group consisting of dimethylformamide (DMF), methylpyrrolidone (NMP), acetonitrile (ACN), dimethylacetamide (DMA), and dimethyl sulfoxide (DMSO).

Meanwhile, in an embodiment of the present invention, the light gas discharged via a pipe through the top of the absorption tower is divided into a second flow 40 and a third flow 50 (see FIG. 1).

The second flow may be a concentrated flow including one or more selected from the group consisting of nitrogen and carbon dioxide, and is circulated along an inner circular line and re-introduced into the reactor. The second flow may further include an unreacted raw material and butadiene as well as nitrogen ($N_2$), carbon dioxide ($CO_2$), and the carbon dioxide included in the second flow may be re-introduced into the reactor to act as a mild oxidant or a diluent gas for oxidative dehydrogenation inside the reactor.

Meanwhile, the third flow is a purge stream and is discharged to an outside of a system through a discharge line separated from the second flow. The third flow may also further include nitrogen (N2), carbon dioxide ($CO_2$), an unreacted raw material, butadiene, and the like.

Meanwhile, in an embodiment of the present invention, the absorption solvent is used to selectively absorb only the C4 mixture including butadiene, but may also dissolve a part of gases, such as nitrogen, carbon dioxide, and the like. Therefore, a degassing step for removing gases, such as nitrogen, carbon dioxide, and the like may be additionally conducted, and the degassing step may be conducted inside a degassing tower.

A degassing method in the degassing step is not particularly limited, and may be performed in a conventional manner used in the technical field.

Refining Step

In an embodiment of the present invention, the C4 mixture including butadiene included in the absorption solvent is converted into high purity butadiene through a refining step. The refining step may include one or more selected from a solvent recovery unit 23 and a butadiene refining unit 24 (see FIG. 1).

In an embodiment of the present invention, when the solvent recovery unit separates and recovers the absorption solvent, the separation and recovery method is not particularly limited, and for example, a distillation separation method may be used. According to the distillation separation method, distillation separation is conducted after the absorption solvent in which the C4 mixture including butadiene is dissolved therein is supplied to the solvent recovery tower by a reboiler and a condenser. When the distillation separation is conducted, a C4 mixture including butadiene is extracted from the vicinity of the top.

The absorption solvent separated in the above process is extracted from the bottom of the solvent recovery tower, and the extracted absorption solvent may be re-supplied to a front end process to be used again. Since the absorption solvent may include an impurity, to the absorption solvent may be subjected to a process of removing an impurity by a known refining method, such as extracting a part before being recycled to perform distillation, decantation, sedimentation, a contact treatment with an absorbent or an ion exchange resin, or the like.

In an embodiment of the present invention, the C4 mixture including a butadiene separated from the absorption solvent may be transferred to the butadiene refining unit 24. In an embodiment of the present invention, high-boiling low-boiling components are removed from the butadiene transferred to the refining tower while the butadiene passes through the butadiene refining unit 24, so that high purity butadiene is produced.

In an embodiment of the present invention, purity of the butadiene finally obtained through the sequence of steps ranges from 99.0 to 99.9%.

Hereinafter, a method of recovering an absorption solvent in a butadiene production process through oxidative dehydrogenation will be described in detail.

Method of Recovering Absorption Solvent

A part of the absorption solvent used in the solvent absorption tower may be included in the light gas separated by the gas separation step, and when the absorption solvent is included in the second flow to be introduced into the reactor, the absorption solvent has a bad influence on oxidative dehydrogenation. Further, when the absorption solvent is discharged to the outside of the system in a state included in the third flow, since the absorption solvent should be again supplied to the solvent absorption tower, economic loss may be caused.

Therefore, to solve the above-described problems, by being provided with a wash column connected to an upper portion of the absorption tower through which the light gas is discharged, the present invention provides a process of recovering the absorption solvent discharged together with the light gas.

Figure 2:
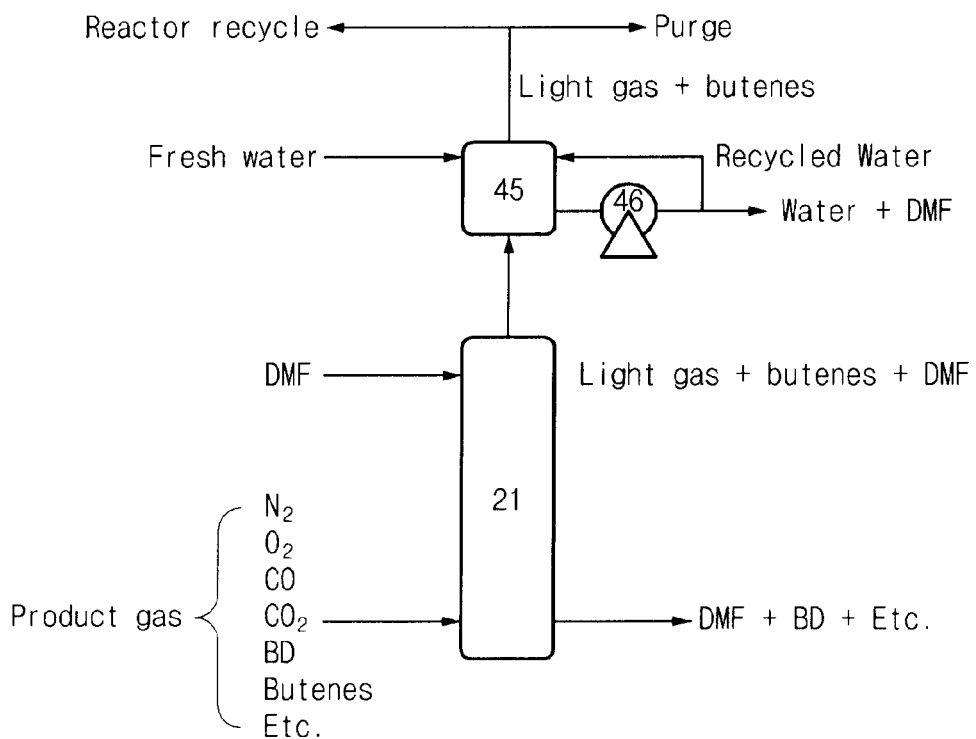
FIG. 2 schematically illustrates an apparatus of recovering an absorption solvent according to an embodiment of the present invention, the apparatus including a wash column connected to an upper portion of a solvent absorption tower.

As an apparatus for the process of recovering the absorption solvent, an embodiment of the present invention provides an apparatus of recovering an absorption solvent, the apparatus including: a pipe through which a light gas is transferred from an upper portion of the absorption solvent column; and a wash column 45 connected to the pipe; a pump 46 provided on one side of the wash column to circulate a solvent introduced into the wash column (see FIG. 2).

Meanwhile, the wash column may be a one or more-stage tray type or a packing type.

A process of recovering the absorption solvent may proceed in the above-described apparatus, and for this, an embodiment of the present invention provides a method of recovering an absorption solvent including the steps of: a) transferring a light gas discharged from an upper portion of an absorption tower to a wash column; and b) recovering an absorption solvent included in the light gas by a solvent circulating in the wash column.

In more detail, the light gas separated from the gas separation step goes up to an upper portion of the absorption tower to be discharged through a pipe, and since the pipe is connected to the wash column, the light gas is subjected to the process of recovering a solvent of the present invention (step a of the present invention)

In addition to gas components including nitrogen, oxygen, steam, carbon monoxide or carbon dioxide among reaction products produced through oxidative dehydrogenation, the absorption solvent used for separating the light gas in the solvent absorption tower may be partially included in the light gas.

Meanwhile, the absorbent solvent that may be partially included in the light gas is a same type as the solvent used in the solvent absorption tower of the gas separation step.

Conventionally, toluene, vinylcyclohexene (VCH) or the like was used as a solvent in the absorption tower in order to absorb most of C4 materials into a lower portion inside the column, and a sponge oil having a relatively higher boiling point than those of the above-described materials for recovering the solvent was used in order to recover the solvent going to the upper portion of the absorption tower along with the light gas. However, such an absorption oil system has a limitation in that there is a possibility the sponge oil having a relatively higher boiling point is included in the recovered light gas to be re-introduced into the reactor, and the re-introduced sponge oil may cause a side reaction.

According to the recovery method according to an embodiment of the present invention, when the light gas reaches the wash column, the light gas comes in gas-liquid contact with the solvent circulating in the wash column, and material exchange takes place by the gas-liquid contact, so that the circulating solvent recovers the absorption solvent included in the light gas (step b of the present invention).

The solvent circulating inside the wash column should have a high affinity to the absorption solvent and also should have no influence on the reaction when being introduced into the reactor. Therefore, the solvent that may circulate inside the wash column may be differently used according to a type of the absorption solvent. An example of the solvent circulating inside the wash column may be a polar protic solvent such as water.

In an embodiment of the present invention, when the absorption solvent is dimethylformamide (DMF), water ($H_2O$) may be used as the solvent circulating inside the wash column, and since water has a high affinity to DMF and also has no influence on oxidative dehydrogenation, water is preferable.

Meanwhile, the solvent circulating inside the wash column should be constantly supplemented, because material exchange may not occur easily when the amount of the solvent circulating inside the wash column is significantly smaller than the light gas. For this, the weight ratio of the light gas to the solvent continuously and newly introduced into the wash column may range from 100:0.1 to 100:10.

Further, since the pump provided in the absorption solvent recovery apparatus allows the solvent introduced into the wash column to be smoothly supplemented, the gas-liquid contact between the light gas and the solvent circulating inside the wash column may be maximized.

In an embodiment of the present invention, a recovery efficiency of the absorption solvent recovered by the method may be 90% or higher.

EXAMPLES

Hereinafter, the present invention will be described below in more detail with reference to embodiments. These embodiments are only provided to illustrate the present invention, and it will be apparent to those skilled in the art that the scope of the present invention is not construed as being limited by these embodiments.

Example 1

In a butadiene production process through oxidative dehydrogenation of the present invention, a light gas discharged from a gas separation device was transferred to a three-stage wash column to recover an absorption solvent. At this time, the absorption solvent used in the solvent absorption tower was DMF. Meanwhile, the amount of fresh water used as a solvent in the wash column was 1,178 kg/h, and the amount of recycle water continuously supplied to the wash column by using a pump was 30,000 kg/hr.

Comparative Example 1

Butadiene was produced by the same method as Example 1, but a process of recovering an absorption solvent with a wash column or the like when a light gas is discharged was not conducted.

Experimental Example 1

As a result of treating the light gas of an upper portion of a solvent absorption tower according to Example 1 and Comparative example 1, a result was obtained as shown in Table 1

TABLE 1

| Mass Flow | Comparative Example 1 (kg/hr) | Example 1 (kg/hr) |
| --- | --- | --- |
| $N_2$ | 113,221 | 113,221 |
| $CO_2$ | 71,413 | 71,405 |
| CO | 308 | 308 |
| $O_2$ | 3,066 | 3,066 |
| 1,3-BD | 500 | 500 |
| Butene | 486 | 486 |
| WATER | 0 | 155 |
| DMF | 106 | 5 |

In the table 1, Example 1 shows a mass flow of a light gas and butene discharged by passing through a wash column, and Comparative example 1 shows a mass flow of a light gas and a butene discharged without passing through the wash column.

Referring to the results of Table 1, it can be confirmed that as in Example 1, the amount of the absorption solvent (DMF) included in the light gas to be discharged in the stream passing through the wash column is remarkably reduced.

The invention claimed is:

1. A method of recovering an absorption solvent used in a process producing butadiene through oxidative dehydrogenation and included in a light gas containing the absorption solvent discharged from an absorption tower during butadiene production, the method comprising:
   a) transferring the light gas containing the absorption solvent discharged from an upper portion of the absorption tower to a wash column;
   b) circulating a circulating solvent having a high affinity to the absorption solvent through the wash column;
   c) introducing the light gas into the circulating solvent in the wash column so that the light gas comes into contact with the circulating solvent, the circulating solvent thereby recovering the absorption solvent from the light gas and producing a separated light gas comprising carbon monoxide or carbon dioxide; and
   d) recycling a part or the whole of the separated light gas to an oxidative dehydrogenation reactor of the process producing butadiene.

2. The method of claim 1, wherein the circulating solvent in the wash column comprises a polar protic solvent.

3. The method of claim 1, wherein the circulating solvent in the wash column is water ($H_2O$).

4. The method of claim 1, wherein, in step b), the circulating solvent is supplemented with fresh solvent, and a weight ratio of the light gas to the fresh solvent in the wash column ranges from 100:0.1 to 100:10.

5. The method of claim 1, wherein the absorption solvent is a polar aprotic solvent.

6. The method of claim 1, wherein the absorption solvent is one or a mixture of two or more selected from the group consisting of dimethylformamide (DMF), methylpyrrolidone (NMP), acetonitrile (ACN), dimethylacetamide (DMA), and dimethyl sulfoxide (DMSO).

7. The method of claim 1, wherein the separated light gas recycled to the reactor further comprises nitrogen.

* * * * *